United States Patent [19]

Tomizawa et al.

[11] Patent Number: 4,922,855
[45] Date of Patent: May 8, 1990

[54] MILKING MACHINE

[75] Inventors: Osamu Tomizawa; Toshiyuki Okatani, both of Nagano, Japan

[73] Assignee: Orion Machinery Co., Ltd., Nagano, Japan

[21] Appl. No.: 197,918

[22] Filed: May 24, 1988

[51] Int. Cl.$^5$ .............................................. H01J 3/00
[52] U.S. Cl. ............................. 119/14.15; 119/14.14; 119/14.08; 73/290 V; 340/606
[58] Field of Search ............... 119/14.08, 14.14, 14.15, 119/14.16, 14.17, 14.18; 340/606; 324/65 R; 73/290 V, 861.08

[56] References Cited

U.S. PATENT DOCUMENTS

| | | | |
|---|---|---|---|
| 3,547,080 | 12/1970 | Russell | 119/14.14 |
| 3,989,009 | 11/1976 | Robar et al. | 119/14.08 |
| 4,292,926 | 10/1981 | Tilman | 119/14.08 X |
| 4,433,577 | 2/1984 | Khurgin et al. | 73/290 V |
| 4,572,104 | 2/1986 | Rubino | 119/14.14 X |
| 4,574,736 | 3/1986 | Tanaka et al. | 119/14.08 |
| 4,616,215 | 10/1986 | Maddalena | 119/14.14 X |
| 4,756,274 | 7/1988 | Rubino | 119/14.08 |
| 4,797,666 | 1/1989 | Baxter et al. | 340/606 |

FOREIGN PATENT DOCUMENTS

| | | | |
|---|---|---|---|
| 3609275 | 9/1987 | Fed. Rep. of Germany | 119/14.14 |
| 56-14247 | 4/1981 | Japan . | |
| 56-46364 | 10/1981 | Japan . | |
| 59-169428 | 9/1984 | Japan . | |
| 1069729 | 1/1984 | U.S.S.R. | 119/14.14 |
| 1175403 | 8/1985 | U.S.S.R. | 119/14.14 |
| 1197614 | 12/1985 | U.S.S.R. | 119/14.14 |

Primary Examiner—Richard J. Apley
Assistant Examiner—Joe H. Cheng

[57] ABSTRACT

A milking machine detects a flow rate of milk during milking and integrates by a completion timer the time when the detected flow rate is smaller than a reference flow rate near an end of the milking, the integrated time being displayed graphically. The reference flow rate is corrected by a specific resistance of milk. The specific resistance is obtained by selecting a minimum resistance value from resistance values of milk which are actually measured during a predetermined time interval starting from a time after milking begins when a flow rate of milk measured on the basis of a predetermined standard resistance value reaches a predetermined value.

6 Claims, 6 Drawing Sheets

MILKING MACHINE

BACKGROUND OF THE INVENTION

1. Field of the Invention

The present invention relates to a milking machine for milking a cow and more particularly to a milking machine capable of measuring a flow rate of milk exactly.

2. Description of the Relevant Art

When a milking machine is employed to milk a cow, it is desirable to finish the milking immediately in view of the protection of the cow and the milking efficiency if the flow rate of milk is smaller than a predetermined value.

Heretofore, the milking operation is finished when a predetermined waiting time elapsed after the detected flow rate of milk is lowered to a predetermined value or less. In this case, Japanese Patent Unexamined Publication No. 59-169428, for example, discloses a finish control apparatus for the milking operation which employs an indicator to display the finish time of the milking operation.

However, the conventional apparatus applies the uniform waiting time to every cow to finish the milking and accordingly there occurs the case where the waiting time is too long or too short depending on characteristics of the cows. The too long waiting time means a long time of milking a cow vainly and affects the cow adversely. Conversely, the too short waiting time leaves milk in the udder of the cow to reduce the milking production and also affects the cow adversely. Thus, it is not possible to control the finish of milking for each cow exactly.

The measurement of the flow rate of milk during the milking is made on the basis of an electrical resistance value between a pair of electrodes provided in a milking line when current flows between the pair of electrodes. The decision to end milking is judged by detecting a resistance value increasing suddenly when the flow rate of milk is reduced to a predetermined value or less near the end of milking and by comparing a resistance value actually measured at this time with a predetermined reference resistance value to detect the reduction of the flow rate of milk.

However, an unusual cow such as a diseased cow with the mastitis generally produces milk having a high electrical conductance and accordingly the actually measured resistance value of milk may be largely different from that of a healthy cow. In this case, the flow rate of milk can not be measured exactly since the reference resistance value is constant, and the finish time of milking deviates from the usual time to further affect the cow adversely.

SUMMARY OF THE INVENTION

It is an object of the present invention to provide a milking machine which determines a time when further milking will be in vain and attains the milking operation with high efficiency and the enhanced protection of a cow so that the end of milking can be controlled exactly for each cow.

Further, it is another object of the present invention to provide a milking machine which indicates graphically the integration time beginning at the time when a flow rate of milk is reduced to a reference value or less at the end of milking so as to be able to easily identify information as to whether the milking has been finished or when the milking is finished at a glance and particularly can determine the time for manual removal of a milking unit easily and exactly.

Furthermore, it is a further object of the present invention to provide a milking machine which can detect the specific resistance of milk of a cow exactly to correct a reference flow rate of milk so that the flow rate of milk can be measured exactly and accurately.

In order to achieve the above objects, according to the present invention, the flow rate of milk is detected during the milking and the time when the actually measured flow rate of milk D1 is reduced to a predetermined reference flow rate of milk D2 or less near the end of the milking is integrated by a completion timer 27, and the integration time is indicated graphically, for example. Further, the reference flow rate of milk D2 is corrected by the specific resistance Ri of milk. The specific resistance Ri is obtained by selecting a minimum resistance Rd from resistance values of milk measured actually for a predetermined period of time Tc from the time when a flow rate of milk measured from the beginning of the milking on the basis of a predetermined standard resistance Ro reaches a predetermined flow rate.

With such a configuration, the integration time for which the actually measured flow rate D1 falls to the reference flow rate D2 or less, more preferably the reference flow rate D2 or less corrected by the specific resistance Ri, is indicated and whether the integration time reaches a predetermined value can be confirmed. Further, since only the time when the actual flow rate of milk is reduced to the reference flow rate of milk D2 or less is integrated, the milking of cows in vain can be prevented.

DETAILED DESCRIPTION OF THE PREFERRED EMBODIMENTS

Figure 1:
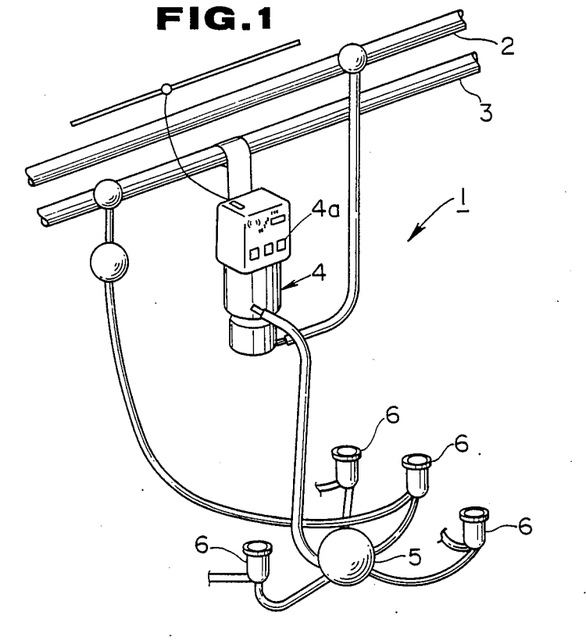
FIG. 1 is a perspective view showing a whole configuration of a milking machine according to the present invention.
Figure 2:
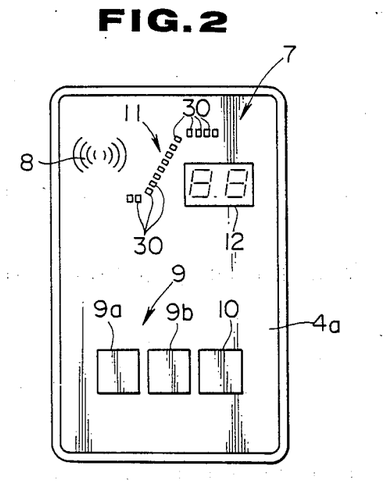
FIG. 2 is a front view of a controller of the milking machine of FIG. 1.
Figure 3:
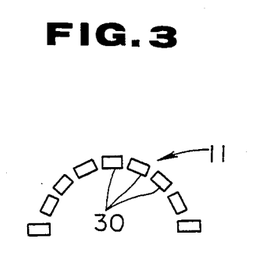
FIG. 3 is a front view of an indicator showing another embodiment in the controller of FIG. 2.

Referring first to FIGS. 1 to 3, the whole configuration of a milking machine 1 according to the present invention is described.

In FIG. 1, numeral 2 denotes a milk pipe and numeral 3 denotes a vacuum pipe. The milk pipe 2 is coupled with a manifold 5 through a controller 4, and four teat cup units 6 are coupled with the manifold 5 and the vacuum pipe 3.

A front panel 4a of the controller 4 is provided, as shown in FIG. 2, with an indicator 7, a loudspeaker 8, a start switch 9 constituted by an automatic start switch 9a and a manual start switch 9b, a stop switch 10, a mode change-over switch not shown and a power switch not shown. The indicator 7 includes an integration time indication portion 11 and a time value indication portion 12 described later in detail. In particular, the integration time indication portion 11 is disposed near the time value indication portion 12 and includes a portion inclined from the lower portion to the upper portion and predetermined horizontal portions at the lower and upper portions so that the indication is easily seen, and a cow can be diagnosed easily. The disposition of the integration time indication portion 11 is not limited to the above embodiment and may be any form. For example, a semicircular form as shown in FIG. 3 is suited as the form of the disposition of the integration time indication portion 11. The integration time indication portion 11 may be divided into a first half and a second half each indicated by different color if necessary.

Figure 4:
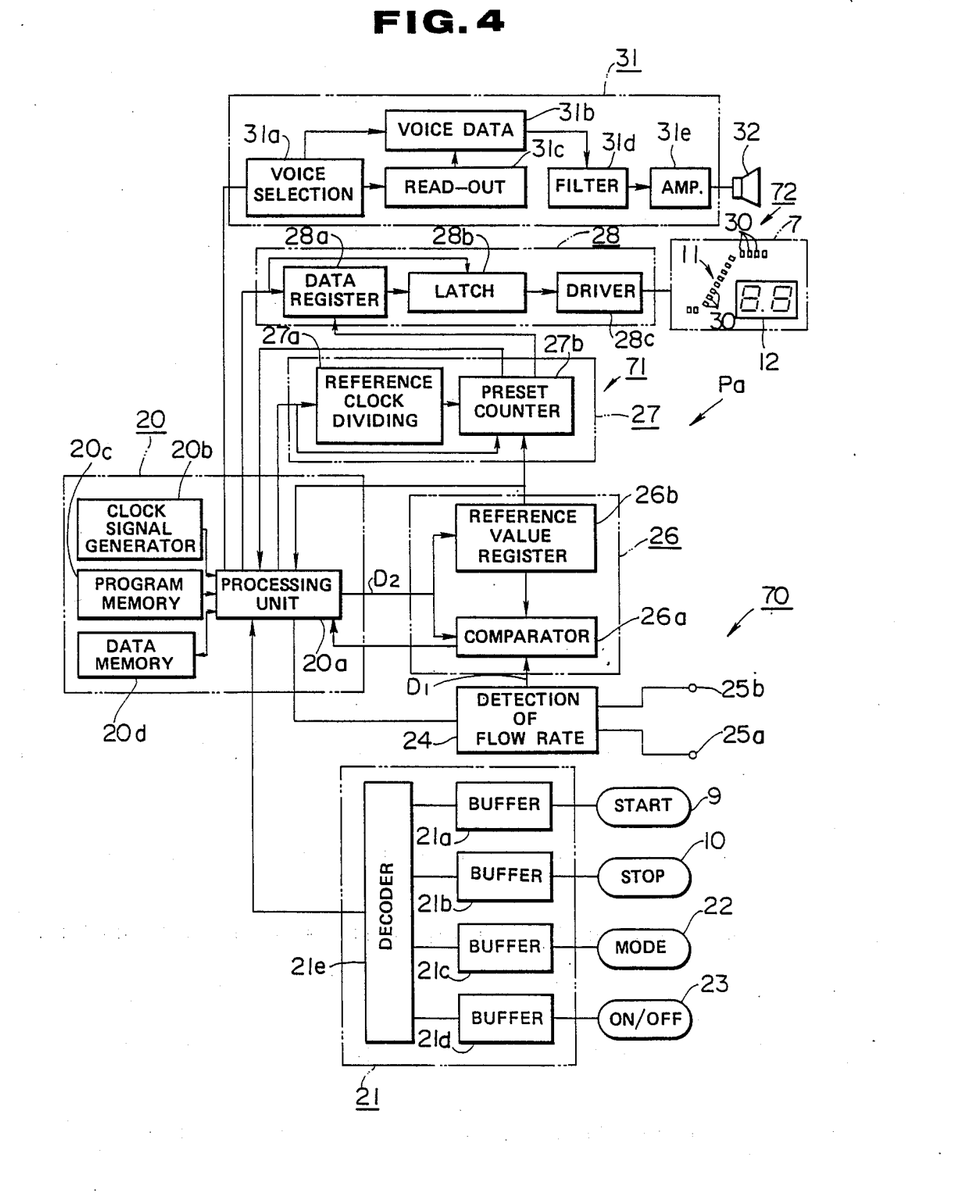
FIG. 4 is a block circuit diagram of an end of milking detection unit in the controller of FIG. 2.

Referring now to the block circuit shown in FIG. 4, a configuration of an end of milking detection unit Pa included in the controller 4 is described.

Numeral 20 denotes a control circuit having a function of a computer and including a processing unit 20a, a clock signal generator 20b, a program memory 20c and a data memory 20d. The control circuit 20 is connected to an operation circuit 21. The operation circuit 21 is connected to the start switch 9, stop switch 10, the mode change-over switch 22 and the power switch 23 described above. The operation circuit 21 includes buffer circuits 21a, 21b, 21c and 21d connected to the switches 9, 10, 22 and 23 and a decoder 21e connected to the buffer circuits 21a to 21d. States of the switches are supplied to the control circuit 20 through the operation circuit 21.

Figure 8:
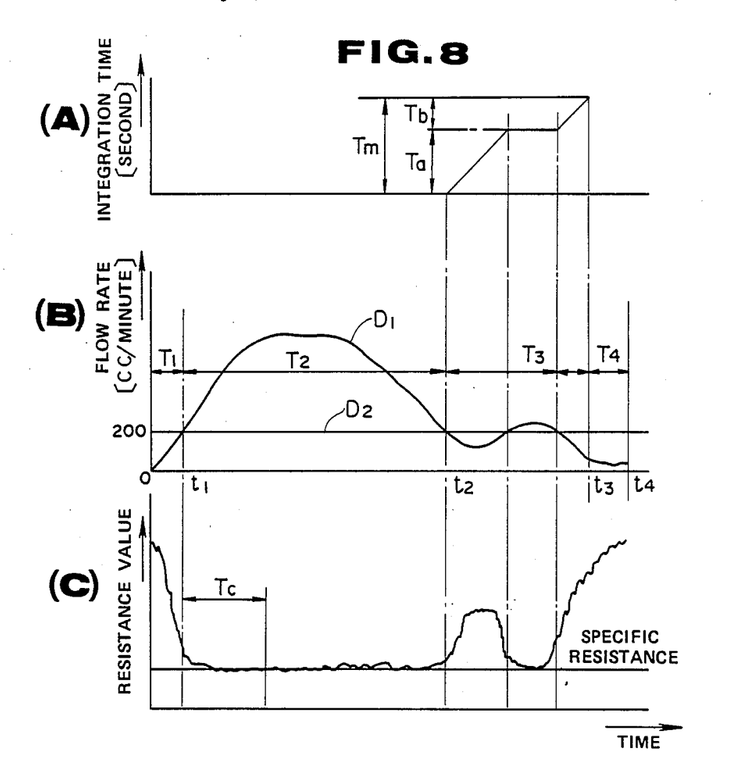
FIG. 8 is a timing chart of each of elements.

Numeral 24 denotes a flow rate detection circuit which is connected to a pair of electrodes 25a and 25b. The electrodes 25a and 25b are disposed in the milking line to measure an electrical resistance of milk by flowing a current between both the electrodes. The measurement can utilizes a method disclosed in, for example, Japanese Unexamined Patent Publication No. 59-169428. The flow rate detection circuit 24 and the electrodes 25a and 25b constitute flow rate detection means 70. The electrical resistance of milk is varied in inverse proportion to the flow rate of milk as shown in FIGS. 8(B) and 8(C). The flow rate detection circuit 24 supplies an actually measured flow rate signal D1 in response to the flow rate of milk to a flow rate comparison circuit 26. The comparison circuit 26 is supplied with a reference flow rate signal D2 previously set in the control circuit 20 and compares the actual flow rate signal D1 with the reference flow rate signal D2. The comparison circuit 26 includes a comparator 26a with an output to the processing unit 20a and a reference value register 26b. The reference flow rate signal D2 is representative of the stable state of the flow rate and is desirably set to a level corresponding to about 200 cc/minute at which the electrical resistance thereof is substantially constant as apparent from FIG. 8(B). Further, the reference flow rate signal D2 is corrected by a detected specific resistance described below so that the flow rate can be measured more exactly.

Figure 6:
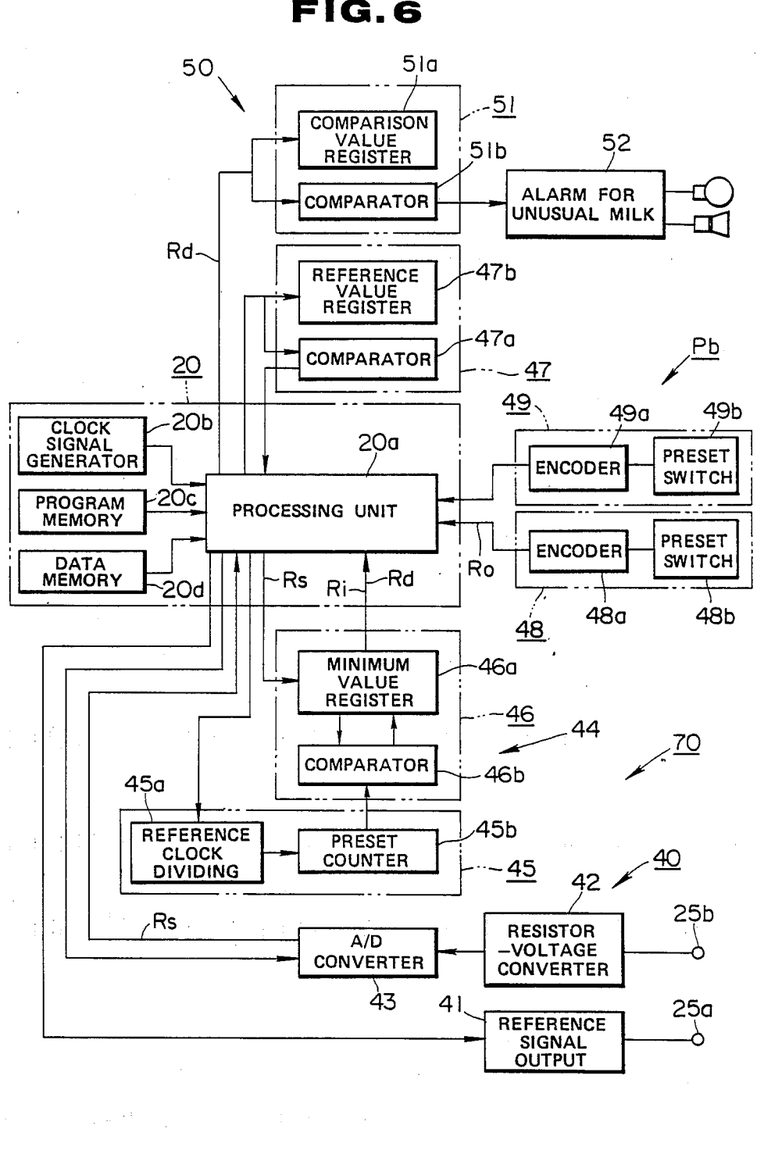
FIG. 6 is a block circuit diagram of a specific resistance detection portion of milk in the controller of FIG. 2.

Referring now to FIG. 6, a specific resistance detection unit Pb provided in the control circuit 20 and the flow rate detection circuit 24 is described in detail. The flow rate detection means 70 is first described in more detail with reference to FIG. 6. A resistance value detection circuit 40 causes a reference signal output circuit 41 to flow a reference current between the electrodes 25a and 25b and to a resistor-voltage converter 42 to measure an electrical resistance between the electrodes 25a and 25b. An output of the converter 42 is supplied to the control circuit 20 through an analog-to-digital converter 43.

A specific resistance detection circuit 44 includes a resistor measuring timer 45 composed of a reference clock division circuit 45a and a preset counter 45b. The timer 45 starts the counting in response to a signal indicating that a flow rate of milk reaches a predetermined flow rate produced from a flow rate comparison circuit 47 and stops the counting when the count reaches a predetermined time Tc (FIG. 8). The flow rate comparison circuit 47 includes a comparator 47a and a reference value register 47b. An operation circuit 46 checks an actually measured resistance Rs (stored in the control circuit 20) obtained from the resistance value detection circuit 40 during the predetermined time Tc to select a minimum resistance value Rd and supplies it to the control circuit 20. The operation circuit 46 includes a minimum value register 46a and a comparator 46b. In this case, the resistance values Rs are measured in the sampling manner at intervals of a fixed time of period during the predetermined time Tc. It is desirable that the interval of the predetermined time Tc is established to the extent that the minimum resistance value Rd can be detected as in FIG. 8.

A standard resistance preset circuit 48 includes an encoder 48a and a preset switch 48b and presets a standard resistance value Ro for a standard cow. A reference flow rate preset circuit 49 includes an encoder 49a and a preset switch 49b and presets the reference flow rate signal D2 (about 200 cc/minute described above). An unusual milk alarm unit 50 supplies the minimum resistance value Rd to an unusual milk comparison and judgment circuit 51 including a comparison value register 51a and a comparator 51b to compare the minimum resistance value Rd with a predetermined threshold value and operates an unusual milk alarm circuit 52 to produce a visual and aural alarm if the minimum resistance value Rd deviates from a normal range.

Figure 7:
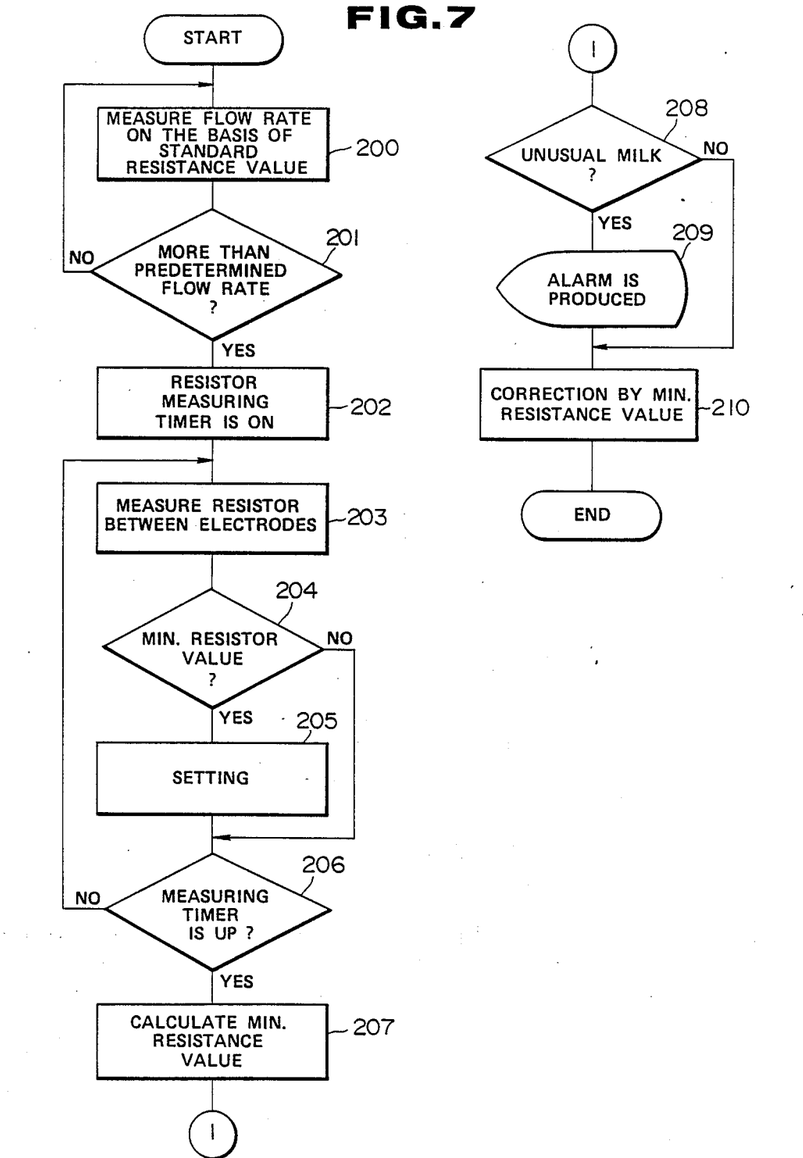
FIG. 7 is a flowchart showing operation of the detection portion of FIG. 6.

The specific resistance value Ri is detected as shown in FIG. 7 by the specific resistance detection unit Pb. When the start switch 9 is turned on, the milking is started and at the same time the reference flow rate signal D2 is set on the basis of the standard resistance value Ro to detect a flow rate of milk (step 200). When the actually measured flow rate D1 exceeds the reference flow rate D2 (200 cc/minute), the resistor measuring timer 45 is operated (steps 201 and 202). At the same time, a resistance between the electrodes is measured continuously until the timer 45 is up and the resistance value is checked to select the minimum resistance value Rd which is sent to the control circuit 20 as the specific resistance value Ri (steps 203, 204, 205, 206 and 207). The unusual milk alarm circuit 52 judges whether the milk is unusual or not on the basis of the minimum resistance value Rd and produces an alarm if it is unusual (steps 208 and 209). Further, the reference flow rate signal D2 is corrected on the basis of the minimum resistance value Rd. More particularly, the standard resistance value Ro previously stored in the control circuit 20 is compared with the specific resistance value Ri and if there is any deviation, a coefficient thereof is calculated to correct the reference flow rate signal D2 (step 210).

Returning to FIG. 4, a completion timer 27 includes a reference clock division circuit 27a and a preset counter 27b and is supplied by the control circuit 20 with a timing signal for starting the operation and a reset signal. Completion timer 27 is supplied with a timing signal for integrating the time from the flow rate comparison circuit 26. The completion timer 27, the control circuit 20 and the flow rate comparison circuit 26 constitute time integration means 71. The completion timer 27 includes a time value measuring timer function which operates from the milking start point. The measured time elapsed is supplied and stored in the control circuit 20 and is displayed by the indicator 7 (FIG. 2) through an indication output circuit 28 including a data register 28a, a latch 28b and an indication driver 28c. These elements constitute indication means 72. The indicator 7 includes the time value indication portion 12 which digitally displays the elapsed time by, for example, a liquid crystal display panel or a fluorescent display tube, and the integration time indication portion 11 including, for example, a plurality of light emitting diodes 30 disposed in a line for integrating and analogically indicating the time of diminished flow at the end of milking. A voice output circuit 31 includes a voice selection circuit 31a, a voice data memory circuit 31b, a read-out circuit 31c, a filter 31d and an amplifier 31e. A loudspeaker 32 is to produce an alarm at a required time described later.

Figure 5:
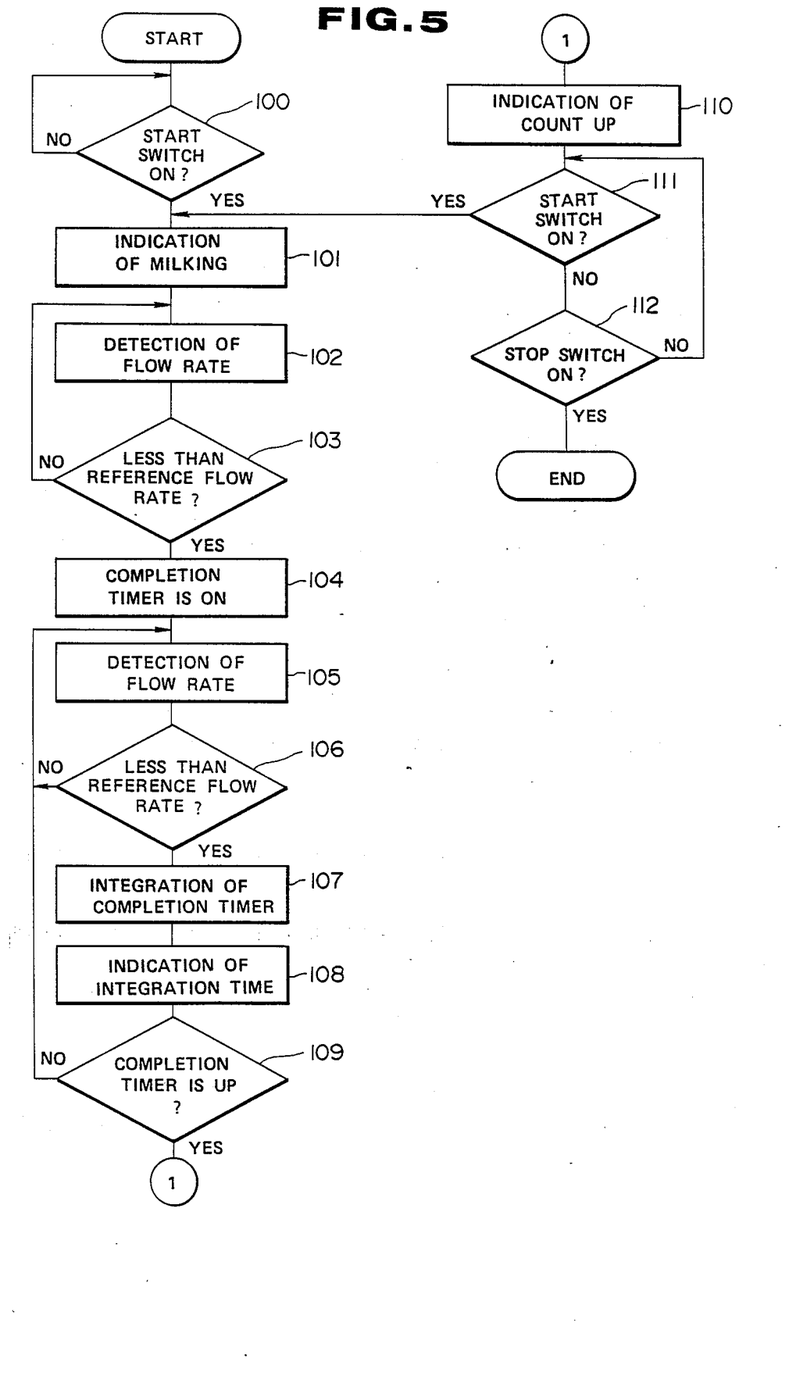
FIG. 5 is a flowchart showing operation of the detection unit of FIG. 4.

Referring now to FIG. 5, the function of the end of milking detection unit Pa is described from the beginning of milking.

When the start switch 9 is turned on, the milking is started. Thus, the specific resistance Ri is detected by the specific resistance detection unit Pb and the necessary correction and supervision are effected. At the same time, in the end of milking detection unit Pa, the time value measuring timer is reset and operates from "0". Further, the indication of milking is also effected (steps 100 and 101). Thus, as shown in FIG. 8(B), milk is increasingly produced with the lapse of time. The electrical resistance value of milk is reduced in response to the production of a milk as shown in FIG. 8(C). The time t1 when the actually measured flow rate D1 corresponding to this resistance value reaches the predetermined reference flow rate D2 is measured and the elapsed time T1 from the beginning of milking is stored. Further, the produced milk is gradually increased and then begins to be decreased after the peak. The time t2 when the actually measured flow rate D1 is reduced to the reference flow rate D2 (corrected by the specific resistance value ri) is measured and the elapsed time T2 from the time t1 is stored. Further, the completion timer 27 is operated at the same time as the time t2 (steps 102, 103 and 104). The timer 27 is operated and integrates the time only when the actual flow rate D1 is smaller than the reference flow rate D2. More specifically, sometimes a cow produces milk again at an increased rate, depending on the characteristic of the cow. In this case a curve of the flow rate of milk is changed as shown in FIG. 8(B) in which the flow rate exceeds the reference flow rate D2 again and is then reduced less than the reference flow rate D2. Accordingly, the completion timer 27 operates during only the time Ta and the time Tb when the actual flow rate D1 is smaller than the reference flow rate D2 as shown in FIG. 8(A) and the integrated time Tm = Ta + Tb is displayed in the integration time indication portion 11 (steps 105, 106, 107 and 108). Thus, when a predetermined time (=Tm) (for example, about 30 seconds) is integrated, the completion timer 27 is up (steps 109 and 110). The indication of the integrated time is effected by turning on the light emitting diodes 30 successively from the lowermost disposed diode in response to the integrated value. Further, the time t3 when the timer 27 is up is measured and the elapsed time T3 from the time t2 is stored. In addition, the voice output circuit 31 serves to produce a preliminary alarm sound, for example, after the lapse of time Ta and to produce an end alarm sound after the timer has been up. The timing when the timer is up can be confirmed by the integration time indication portion 11 and accordingly the stop switch 10 is depressed to reset the indication of time (steps 111 and 112). The stop time t4 is measured and the elapsed time T4 from the time t3 is stored. At the same time the time T1 is displayed by the integration time indication portion 11. The elapsed time T4 is the over-milking time.

Generally, for removing the teat cup units 6 of the milking machine 1 from the teats of the cow, there are manual and automatic methods. When the teat cup units 6 are automatically removed, there is a case where there may be no elapsed time T4. When the mode changeover switch 22 is successively operated without turning off the power switch 23, the time T2 to T4 can be displayed by the time value indication portion 12 and the total time can be also displayed if desired.

Figure 9:
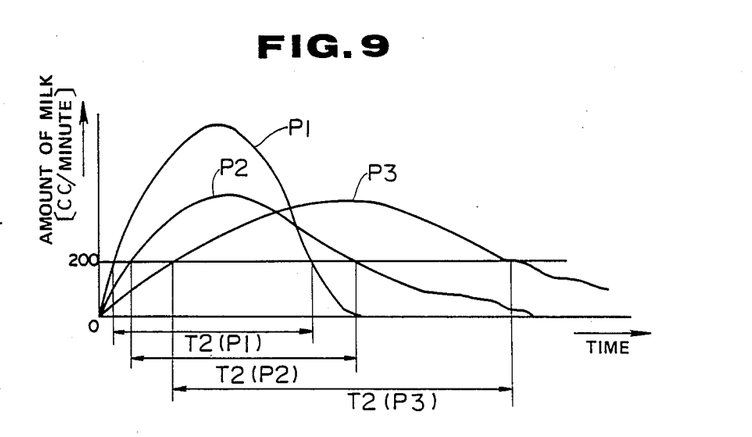
FIG. 9 is a characteristic diagram of an output of milk for each cow in respect to time.

The relation between the milking time and the amount of milk is as shown in FIG. 9, in which the amount of milk produced from a superior cow shown by a curve P1 increases early and decreases to complete the production of milk early. Curves P2 and P3 show the amount of milk produced from an average healthy cow and a cow which is not so healthy, respectively. When a cow is not so healthy, the flow rate of milk increases and decreases slowly to complete the production of milk late. Accordingly, the time T1 to T2, further T3 and T4 are compared with the predetermined time values so that the characteristics of the cow can be diagnosed.

The present invention is not limited to the embodiment described above. The circuit thereof may be an electric circuit or may be realized by a microcomputer and appropriate software. Further, while the minimum resistance is detected to correct the reference flow rate, the actually measured resistance may also be corrected. In addition, structure, configuration, arrangement and numerical values may be changed without departing from the spirit of the present invention.

We claim:

1. A device for measuring and controlling flow rate of a milk in a milking machine, said device comprising:
   a pair of electrodes disposed in a milk flow line during a milking process;
   flow rate detection means for supplying a reference current between said electrodes, detecting an electrical resistance value btween said electrodes, said detected resistance value is represented a measured flow rate of milk, and from said detected resistance value developing a signal representing said measured flow rate of milk;
   time integration means for integrating an elapsed time near an end of the milking process when the measured flow rate of milk is at a diminished level;

said time integration means including a timer for calculating said integrated elapsed time, comparing said integrated elapsed time to a predetermined elapsed time and producing a completion alarm, said timer operates in response to said signal from said flow rate detection means when said measured flow rate of milk is less than a predetermined reference flow rate; and display means for displaying said integrated elapsed time obtained from said time integration means.

2. The device for measuring and controlling flow rate of a milk in a milking machine according to claim 1, wherein said display means includes a time value indication portion configured to display said elapsed time during the milking process when the measured flow rate of milk is below the predetermined reference flow rate of milk.

3. The device for measuring and controlling flow rate of a milk in a milking machine according to claim 1, and further comprising a specific resistance detection circuit for evaluating the minimum resistance value from said detected resistance values between said electrodes during a predetermined time interval and selecting a specific resistance of milk which is initiated when said measured flow rate of milk first exceeds the predetermined reference flow rate of milk, and means for generating a reference flow rate signal which is based on said specific resistance of milk.

4. The device for measuring and controlling flow rate of a milk in a milking machine according to claim 3, wherein the specific resistance of milk is equal to the detected minimum resistance value.

5. The device for measuring and controlling flow rate of a milk in a milking machine according to claim 3, and further comprising:

an unusual milk comparison circuit for comparing the detected minimum resistance value with a predetermined threshold value and generating an alarm signal when the difference between said compared resistance value deviates from a normal range; and an unusual milk alarm producing circuit for producing an alarm in response to said alarm signal.

6. The device for measuring and controlling flow rate of a milk in a milking machine according to claim 1, wherein said display means comprises an integration time indication portion for displaying graphical indication.

* * * * *